US005693484A

United States Patent [19]
Nakamoto et al.

[11] Patent Number: 5,693,484
[45] Date of Patent: Dec. 2, 1997

[54] METHOD OF CLASSIFYING AND COUNTING CELLS IN URINE

[75] Inventors: Hiroyuki Nakamoto; Chiyose Fujiwara, both of Hyogo-ken, Japan

[73] Assignee: TOA Medical Electronics Co., Ltd., Hyoko-ken, Japan

[21] Appl. No.: 329,662

[22] Filed: Oct. 26, 1994

Related U.S. Application Data

[63] Continuation of Ser. No. 881,514, May 12, 1992, abandoned.

[30] Foreign Application Priority Data

May 14, 1991 [JP] Japan .................... 3-109267

[51] Int. Cl.$^6$ .................... G01N 15/10; G01N 21/47; G01N 21/64
[52] U.S. Cl. .................... 435/39; 435/7.24; 435/7.25; 435/29; 435/38; 436/52; 436/63; 436/66; 436/172; 436/800; 356/73; 356/336; 356/338; 356/417; 250/461.2; 209/581; 209/582
[58] Field of Search .................... 435/29, 34, 38, 435/7.21, 7.24, 7.25, 7.32, 39; 436/172, 52, 63, 66, 800; 356/72, 73, 317, 336, 338, 417; 250/461.2; 209/580, 581, 582, 939

[56] References Cited

U.S. PATENT DOCUMENTS

| | | | |
|---|---|---|---|
| 3,899,297 | 8/1975 | Hirschfeld | 436/172 |
| 4,263,508 | 4/1981 | Leary et al. | 250/358.1 |
| 4,336,029 | 6/1982 | Natale | 436/172 |
| 4,338,024 | 7/1982 | Bolz et al. | 356/23 |
| 4,559,309 | 12/1985 | Evenson | 436/172 |
| 4,622,298 | 11/1986 | Mansour et al. | 435/34 |
| 4,661,913 | 4/1987 | Wu et al. | 364/500 |
| 4,859,584 | 8/1989 | Hovan | 436/172 |
| 4,957,870 | 9/1990 | Lee | 436/172 |
| 5,039,613 | 8/1991 | Matsuda | 436/172 |
| 5,075,556 | 12/1991 | Fan | 436/172 |
| 5,325,168 | 6/1994 | Nakamoto et al. | 356/73 |
| 5,325,169 | 6/1994 | Nakamoto et al. | 356/73 |

FOREIGN PATENT DOCUMENTS

| | | |
|---|---|---|
| 0 008 826 | 3/1980 | European Pat. Off. . |
| 0259833 | 8/1987 | European Pat. Off. . |
| 0 333 560 | 9/1989 | European Pat. Off. . |
| 0 347 039 | 12/1989 | European Pat. Off. . |
| 3544867 | 11/1986 | Germany . |

OTHER PUBLICATIONS

Eisert, et al. Analytical and Quantitative Cytology. vol. 3 N. 1, 1981 pp. 17–20.

Investigative Urology, vol. 13, No. 5, 1976, Baltimore, USA, pp. 331–338, M. R. Malamed et al.: Urinary Cytology Automation: Preliminary Studies with Acridine Orange Stain and Flow–Through Cytofluorometry.

Science, vol. 220, May 6, 198, Lancaster, PA USA, pp. 620–622; M. A. Van Dilla et al.: Bacterial Characterization by Flow Cytometry.

*Primary Examiner*—Milton Cano
*Attorney, Agent, or Firm*—Pearne, Gordon, McCoy & Granger LLP

[57] ABSTRACT

A reagent for analyzing cells in urine and a method for analyzing cells in urine with the use of the reagent are provided. The present invention discloses a reagent for analyzing cells in urine which comprises solution(s) containing a fluorescent dye, an osmolarity compensating agent and a buffer, as well as a method for analyzing cells in urine which comprises diluting a urine sample and staining cells therein with the reagent, irradiating the cells with light in the violet or blue wavelength region by using a flow cytometer and measuring the forward or side scattered light and fluorescence from the cells.

9 Claims, 5 Drawing Sheets

ERYTHROCYTE

FORWARD SCATTERED LIGHT

FORWARD FLUORESCENCE

Fig. 3

LEUKOCYTE

FORWARD SCATTERED LIGHT

FORWARD FLUORESCENCE

BLOOD CAST

FORWARD SCATTERED LIGHT (a)
(b)

FORWARD FLUORESCENCE

METHOD OF CLASSIFYING AND COUNTING CELLS IN URINE

This is a continuation of application Ser. No. 07/881,514, filed May 12, 1992 now abandoned.

BACKGROUND OF THE INVENTION

1. Field of the Invention

This invention relates to a method for optically analyzing cells in urine with flow cytometry. More particularly, it relates to a method for analyzing cells in urine wherein cells contained in urine are detected and classified with the use of a fluorescent dye capable of giving stable fluorescent signal waves by using a reagent so as to maintain the pH value and osmotic pressure of a specimen to be analyzed each at a definite level, regardless of the pH value and osmotic pressure of a urine sample.

2. Description of the Prior Art

Detection of cells contained in urine is a basic and important clinical test which have been carried out in all sorts of clinics and laboratories, since information on various diseases including renal/urinary infections, inflammatory lesions, denatured lesions, lithiasis and tumors can be obtained thereby.

Examinations of the contents of urine have been performed for a long time and are still highly important. For example, renal disorders can be screened by examining erythrocytes, leukocytes, epithelial cells and blood casts contained in urine. The determination of erythrocytes is important in detecting hemorrhage in the pathway from the renal glomeruli to renal tract. The appearance of leukocytes is highly important in the diagnosis of inflammation and infection at the early stage, since it suggests the possibility of the outbreak of renal diseases such as pyelonephritis. On the other hand, examination on the morphology of blood casts or erythrocytes makes it possible to estimate the origin thereof, namely, the abnormal site.

Known methods for analyzing cells contained in urine include:

a) microscopic observation; and
b) automated measurement with the use of a combination of a flat sheath flow and image processing techniques (refer to Japanese Patent Laid-Open No. 500995/1982 or U.S. Pat. No. 4,338,024).

In the above-mentioned method a), a urine sample is centrifuged, the obtained sediment is prepared into a slide specimen and then physical components contained therein are classified and counted under a microscope.

This method a) suffers from some problems such that troublesome pretreatments including centrifuging and staining are required; that cells are damaged during the centrifuging step; and that the degree of concentration varies from case to case. In practice, microscopic observation is a great burden for a technical and, furthermore, only a small number of cells can be observed, which makes the obtained classification and counting data less accurate. It is, therefore, urgently required to establish an automated examination system.

The patents cited regarding the method b) disclose a device wherein a urine sample, which is formulated into an extremely flat flow with the use of a sheath fluid as an external layer, is photographed with a video camera and the stationary image thus obtained is processed so as to take out and display physical components contained in the sample.

A urinary sediment contains some components, though in a small amount, the detection of which is highly important. Blood casts may be cited as an example of such components. In general, a urine sample contains only several tens per ml of blood casts. Therefore, it is sometimes observed that an important component (i.e., blood casts) cannot be found when the number of samples is limited. This problem is common to both of the methods a) and b). The method b) further suffers from additional disadvantages such that the automated device for image processing per se is very expensive and that the processing speed is low. Although this device is an automated one, it can only roughly classify the photographed components depending on size and display the image. Namely, the classification treatment must be carried out by manual operation by reference to the displayed image. That is to say, there has been developed no device so far by which components can be automatically classified and counted.

As discussed above, these conventional methods require a high expenditure of time and labor for pretreatments (centrifuging and concentration) of urine samples and the visual observation following the staining. In addition, it is difficult to preserve urine samples for a long time. Thus these methods are unsuitable for the analysis of a large number of samples.

In addition, the examination results vary from laboratory to laboratory, since there has been established no standard criteria so far.

Further, only a limited number of cells can be visually observed in the conventional methods, which results in a low degree of accuracy. Furthermore, judgment should be effected by those skilled in the art.

Accordingly, it is an object of the present invention to establish a method for rapidly, accurately and quantitatively analyzing cells in a urine sample and to provide a reagent to be used in said method.

SUMMARY OF THE INVENTION

In order to overcome the above-mentioned disadvantages of the conventional methods, the present invention provides a method for automatically, rapidly and accurately measuring cells in urine by flow cytometry and for analyzing, involving classifying, the cells in urine as well as a reagent to be used in said method.

More particularly, the present invention relates to a reagent, which comprises a sufficient amount of a fluorescent dye and a buffer and an osmolarity compensating agent for stabilizing the intensity of fluorescence in optical measurement, as well as a method for analyzing cells in urine by flow cytometry with the use of said reagent, which comprises diluting urine, clearly and strongly staining maleic acids in cells contained in urine, irradiating said cells with light in the violet or blue wavelength region and measuring the fluorescence and scattered light from said cells.

In these figures, each symbol has the following meaning.

1: bacteria,

2: erythrocytes,

3: leukocytes,

4: epithelial cells,

5: glass blood casts,

6: other blood casts,

10: argon ion laser,

12: exit light,

14: dichroic mirror,

16: dichroic mirror,

18: condenser lens,

20: flow cell,

21: cells,

22: nozzle,

23: photodiode,

24: photomultiplier, (a) threshold of strong fluorescence intensity, (b) threshold of medium fluorescence intensity, (A) leukocytes, (B) epithelial cells.

DETAILED DESCRIPTION OF THE INVENTION

The term "cells" to be used here involves erythrocytes, leukocytes, epithelial cells, blood casts and bacteria. Among cells contained in urine, erythrocytes and leukocytes are about 10 μm in size. Epithelial cells are larger than blood corpuscles and show an extremely wide distribution range. Some blood casts are about 100 μm in size, though they usually have a size of several hundreds μm. Bacteria are smaller than them.

Thus urine contains various cells differing in size from each other. Further, it is considered that these cells are seriously damaged. Accordingly, it has been considered that cells contained in urine cannot be analyzed by flow cytometry. It is certainly difficult at present to analyze cells in urine in detail, for example, classifying blood casts into groups. However the present inventors have directed their attention to the possibility of flow cytometry as a means for screening and, after trial and error, successfully completed the present invention.

The reagent to be used in the present invention contains a fluorescent dye. It is therefore needed to maintain the pH value and osmotic pressure of a sample to be analyzed each at a definite level so as to stabilize the fluorescence intensity. Compared with blood, the normal data of urine widely varies, as Table 1 shows. When a blood sample is to be analyzed by flow cytometry, the sample, which contains a large number of cells, is diluted several hundred-fold with a reagent. Therefore, the pH value and osmotic pressure of the sample are scarcely changed. When an urine sample is to be analyzed, on the other hand, the dilution ratio with a reagent cannot be so elevated by taking the accuracy into consideration, since the urine sample contains far fewer cells than a blood sample. However the pH value and osmotic pressure of urine widely vary, compared to blood. When the dilution is insufficient, therefore, the pH value and osmotic pressure of the sample varies. As a result, no stable fluorescence intensity is achieved and, therefore, the obtained data has a low degree of accuracy.

In the present invention, accordingly, a buffer and an osmolarity compensating agent are added to the reagent so as to suppress the variation of the pH value and osmotic pressure of a sample even at a low dilution ratio.

The reagent of the present invention may comprise one or more fluorescent dyes preferably selected from among those cited below:

Auramine O;

Acridine Orange;

ethidium bromide;

propidium iodide;

Neutral Red:

Basic Yellow 11;

Acridine Red

Rhodamine S;

Rhodamine 6G;

Rhodamine B;

Rhodamine 19 perchlorate;

Rhodamine 123;

Eosin Y;

Cyanosine;

Cresyl Fast Violet;

Darrow Red;

Acronol Phloxine 3,3'-dimethylthiocarbocyanine;

3,3'-diethylthiocarbocyanine;

3,3'-diethyl-9-methylthiocarbocyanine bromide;

2-[γ-(1'-ethyl-4',5'-benzothiazolylidene)propenyl]-3-ethyl-4,5-benzoxazolium iodide;

Astrazon Red 6B;

Basic Violet 16;

2-(p-dimethylaminostyryl)-3-ethyl-4,5-benzothiazolium iodide;

2,4-bis(p-dimethylaminostyryl)-1-ethyl-pyridinium iodide;

2,8-bis(p-dimethylaminostyryl)-1-ethyl-pyridinium iodide; and

Astrazon Orange R.

These fluorescent dyes would be specifically bound nucleic acids in cells thus fluorescent-staining the cells.

The osmolarity compensating agent to be used in the reagent of the present invention may be selected from among those cited below:

lithium chloride;
sodium chloride;
potassium chloride;
ammonium chloride;
sodium propionate;
phosphates; and
carbonates.

The buffer to be used in the reagent of the present invention may be selected from among those cited below:

phosphoric acid (salt) series buffers;
phthalic acid (salt) series buffers;
citric acid (salt) series buffers;
boric acid (salt) series buffers;
acetic acid (salt) series buffers;
maleic acid (salt) series buffers;
Tris series buffers;
Tricine series buffers;
glycylglycine series buffers;
dimethylglycine series buffers;
diglycolic acid series buffers;
taurine series buffers; and
Barbital (salt) series buffers.

The reagent of the present invention may be in the form of an aqueous solution comprising the above-mentioned fluorescent dye, buffer and osmolarity compensating agent. However it is preferably in the form of a two-pack or three-pack system in order to achieve stable storage of the components.

A two-pack type of formulation may comprise:

(fluorescent dye+buffer) and (osmolarity compensating agent);

(fluorescent dye) and (buffer+osmolarity compensating agent); or (fluorescent dye+osmolarity compensating agent) and (buffer).

On the other hand, a three-pack type of formulation may comprise, for example,:

(fluorescent dye), (buffer) and (osmolarity compensating agent); or (fluorescent dye 1), (fluorescent dye 2) and (buffer osmolarity compensating agent).

In the method for analyzing cells in urine of the present invention, a urine sample obtained from a subject (original urine) is first diluted from 2- to 20-fold (urine sample: reagent=1:1 to 1:19).

The lower limit of the dilution ratio as specified above (i.e., 2-fold) is the minimum level capable of maintaining the pH value at a definite level throughout the measurement. As Table 1 shows, the pH value of urine widely varies. When a fluorescent dye is directly added to the original urine, the pH value would vary during the measurement. As a result, a stable intensity of fluorescence cannot be obtained. It is therefore required to dilute the original urine with a reagent containing a buffer. The reagent (pH 8.5) employed in the Example as will be given below makes it possible to adjust the pH value of a urine sample (pH 4.5) to 8.0 and to 8.5 respectively at dilution ratios of 2 and 3 or above. The pH value can be more strictly controlled to a level suitable for each fluorescent dye by appropriately selecting the type and concentration of a buffer.

The upper limit of the dilution ratio as specified above (i.e., 20-fold) is determined based on the number of particles to be analyzed. As Table 1 shows, urine contains a considerably small number of cells. In order to maintain accuracy at a definite level, the dilution ratio cannot be extremely elevated. Thus the upper limit of 20-fold is determined by taking the analytical capacity and performance (number of samples treated within unit time) of an instrument and reproducibility into the consideration.

In the method of the present invention, the diluted urine sample is employed as a specimen and the forward scattered light or side scattered light of each cell contained therein is detected by flow cytometry. Then the pulse width of the signal is determined and regarded as corresponding to the cell size. Thus blood corpuscles are separated from other components depending on the difference in pulse width and counted. Next, the blood corpuscles are further divided into erythrocytes and leukocytes depending on the difference in fluorescence intensity. Thus erythrocytes, leukocytes and other components of urine can be assayed.

As the fluorescence, either forward fluorescence or side fluorescence may be employed.

The method of the present invention is further characterized in that the peak numbers of scattered light are determined and erythrocytes, leukocytes, epithelial cells, blood casts and bacteria are classified and counted with the use of parameters of scattered light intensity, scattered light pulse width, scattered light peak number and fluorescence intensity.

Now the present invention will be illustrated in greater detail by reference to the attached figures.

Figure 1:
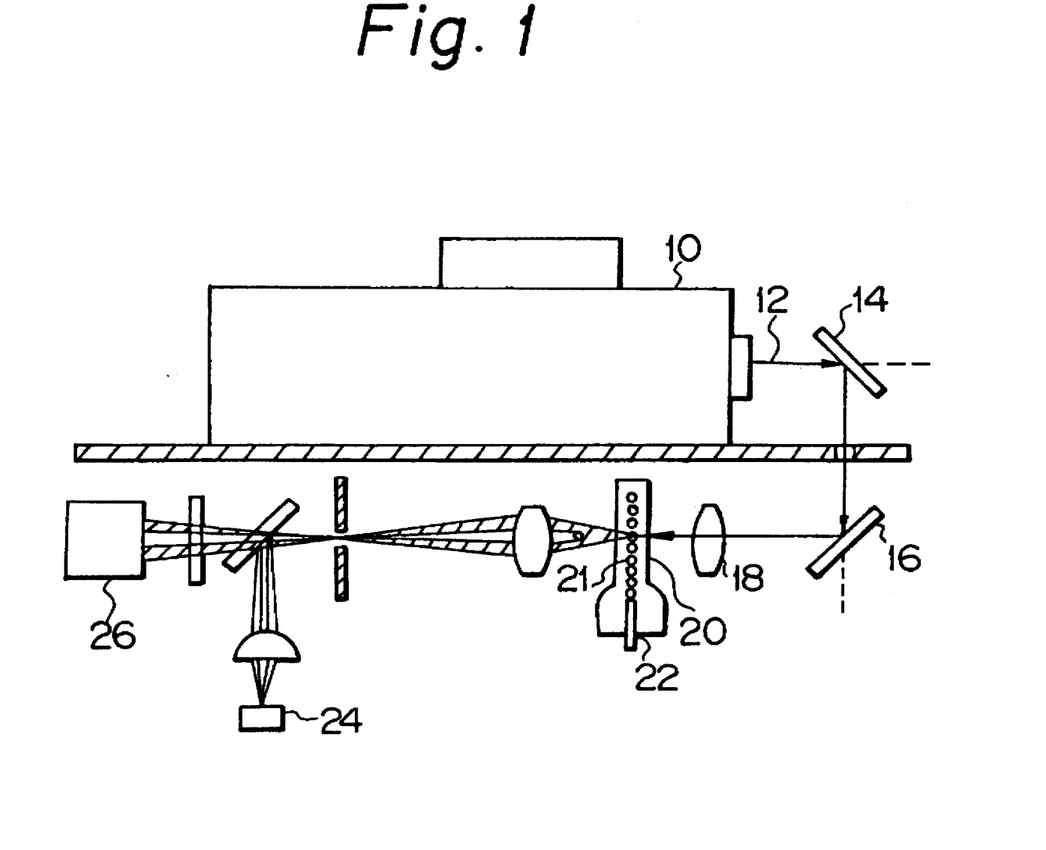
FIG. 1 is a side view of the major part (a detection unit) of a flow cytometer to be used in the present invention.
Figure 2:
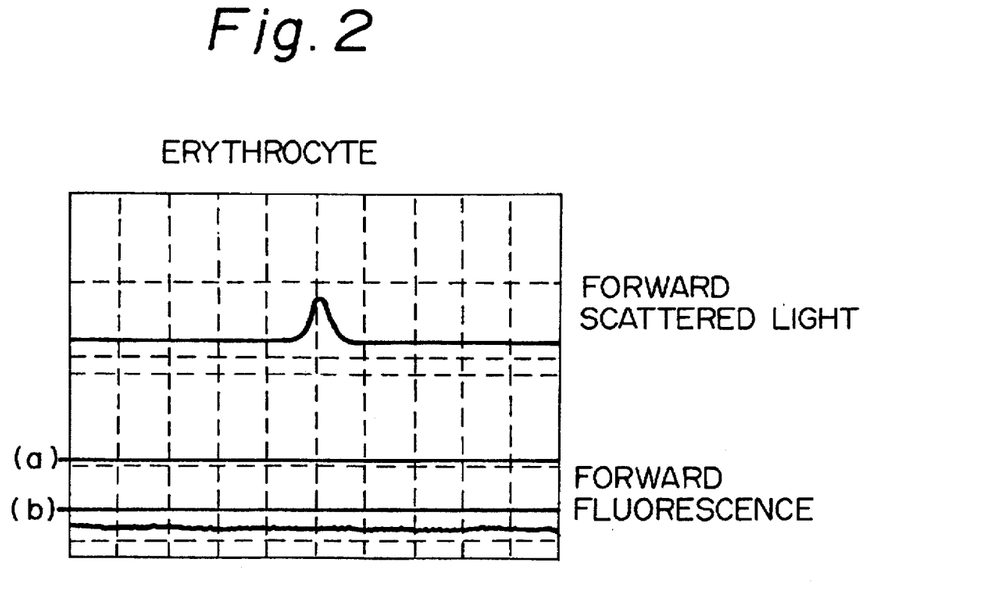
FIG. 2 is an output wave chart showing the signal wave of forward scattered light and the signal wave of forward fluorescence from erythrocytes in urine obtained by using a reagent which comprises Auramine O as a fluorescent dye and adjusting the pH to 8.5 with a buffer.
Figure 3:
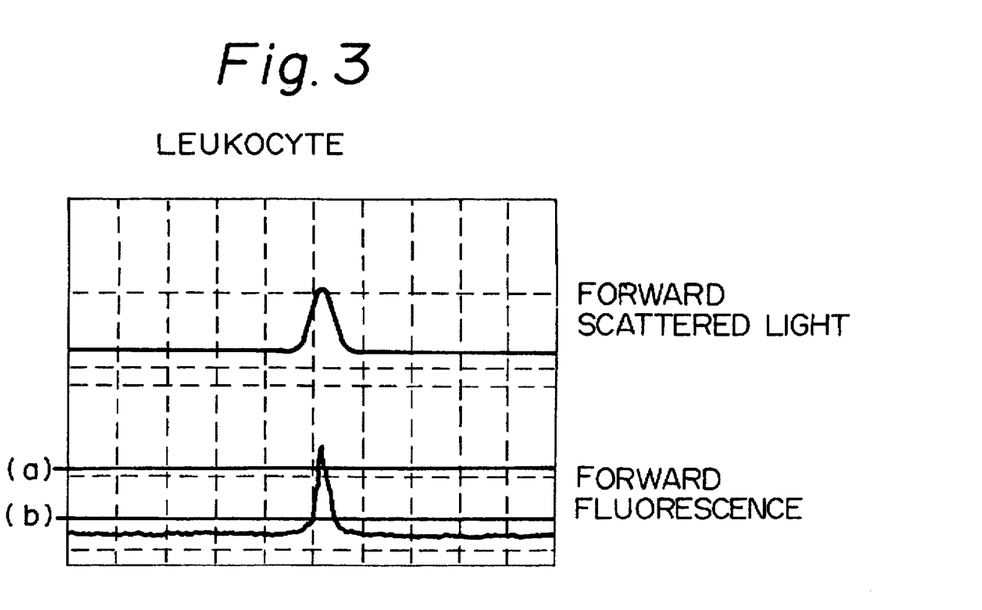
FIG. 3 is an output wave chart showing the signal wave of forward scattered light and the signal wave of forward fluorescence from leukocytes in urine obtained by using a reagent which comprises Auramine O as a fluorescent dye and adjusting the pH to 8.5 with a buffer.
Figure 4:
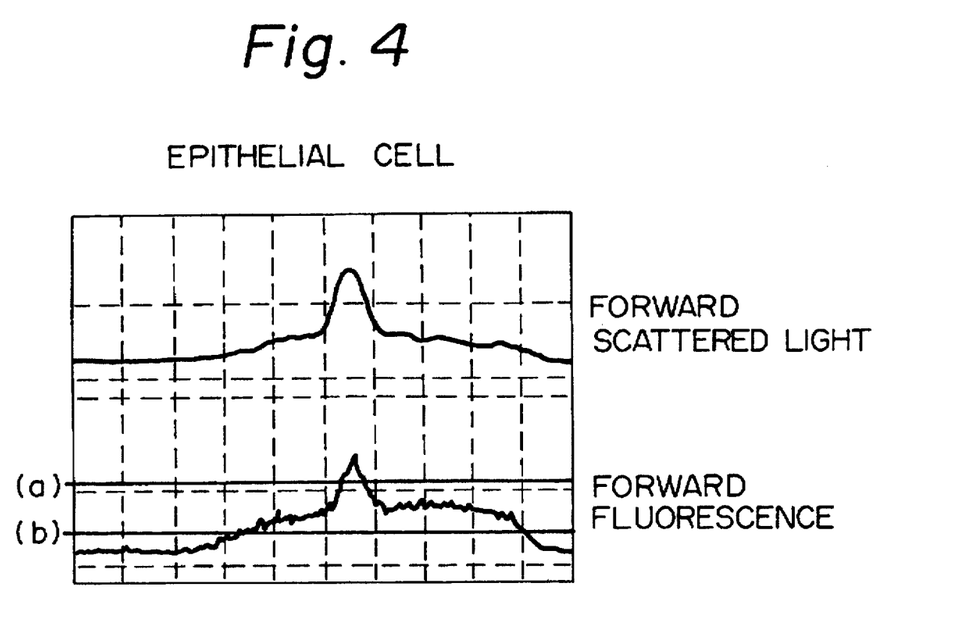
FIG. 4 is an output wave chart showing the signal wave of forward scattered light and the signal wave of forward fluorescence from epithelial cells in urine obtained by using a reagent which comprises Auramine O as a fluorescent dye and adjusting the pH to 8.5 with a buffer.
Figure 5:
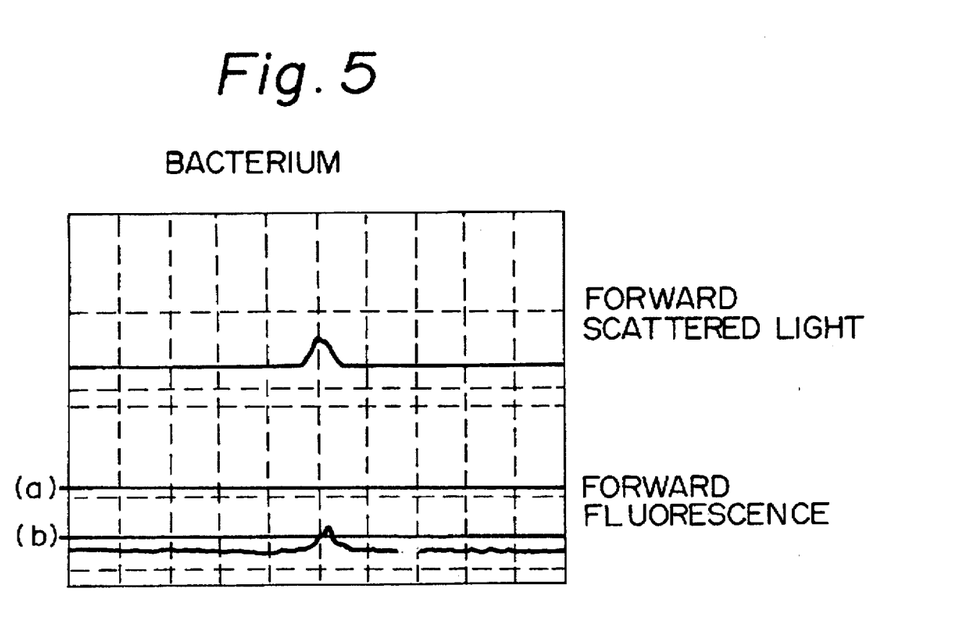
FIG. 5 is an output wave chart showing the signal wave of forward scattered light and the signal wave of forward fluorescence from bacteria in urine obtained by using a reagent which comprises Auramine O as a fluorescent dye and adjusting the pH to 8.5 with a buffer.
Figure 6:
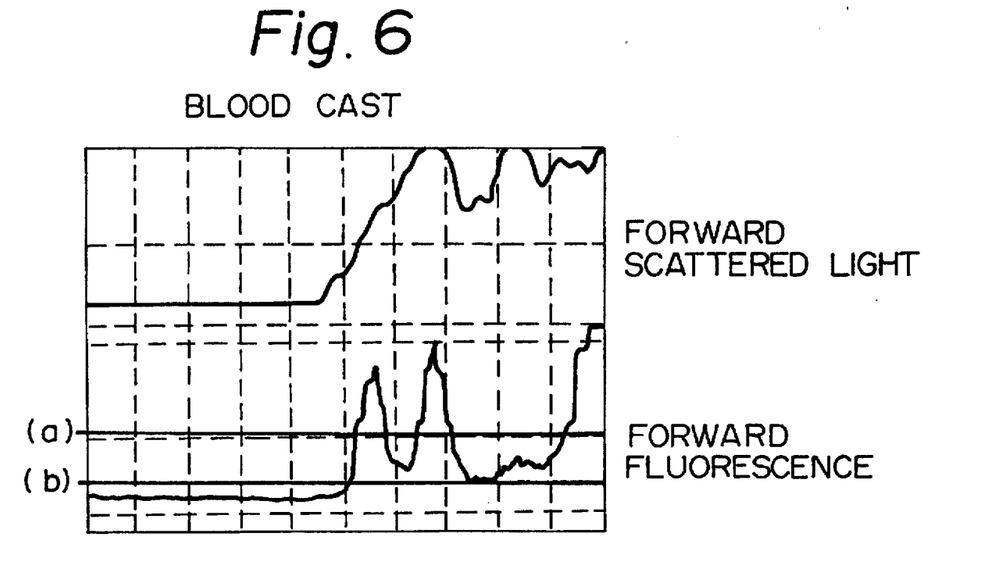
FIG. 6 is an output wave chart showing the signal wave of forward scattered light and the signal wave of forward fluorescence from blood casts (enclosing leukocytes or small-size epithelial cell therein) in urine obtained by using a reagent which comprises Auramine O as a fluorescent dye and adjusting the pH to 8.5 with a buffer.

FIG. 1 is a side view of the main part (detection unit) of a device to be used for measuring cells in urine. This device is a flow cytometer A specimen to be assayed, which has been fluorochrome-stained, is discharged from a nozzle 22. A sheath fluid is flown around the specimen so as to form a sheath flow. Cells 21 contained in urine flow in line in the center of a flow cell 20.

The exit light beams 12 from an argon ion laser 10 are reflected upon dichroic mirrors 14 and 16. Finally, a beam of a wavelength 488 nm alone reaches the flow cell 20. On the other hand, beams of other wavelength pass through the dichroic mirrors. 18 is a condenser lens. Light is irradiated to the region of the sample cells in the form of an ellipse having the minor axis in the direction of the flow and the major axis perpendicular to the flow. In order to obtain detailed information from the cells in urine, the condenser lens to be used in the method of the present invention preferably has a thickness relatively smaller than the size of physical components. The minor diameter of the lens preferably ranges from 1 to 20 μm regarding the irradiation light at the fine stream of the specimen. On the other hand, the major diameter may sufficiently exceed the width of the specimen fine flow. The scattered light and fluorescence from a cell are detected and measured respectively by a photodiode 24 and a photomultiplier 26. In the following Example, forward scattered light and side fluorescence were employed.

As Table 1 shows, urine considerably differs from blood as a test sample.

TABLE 1

Comparison of normal data of urine and blood

|  | Urine | Blood |
|---|---|---|
| pH | 4.5–8.0 (average: 6.0) | 7.4 |
| Osmotic pressure (m Osm/kg H$_2$O) | 50–1,300 | 275–290 |
| Cell count: | | |
| Erythrocyte | <1,000/ml | 395–510 × 10$^4$/µl |
| Leukocyte | <1,500/ml | 5,300–7,900/µl |
| Epithelial cell | <500/ml | 11–34 × 10$^4$/µl |
| Blood cast | <100/ml | |

That is to say, the pH value (from 4.5 to 8.0) and the osmotic pressure (from 50 to 1300 Osm/kg H$_2$O) vary over a considerably wide range. The fluorescence intensity of a fluorescent dye largely varies depending on pH value. It is therefore needed to maintain the pH value at a definite level in order to obtain a stable fluorescence intensity. Thus a urine sample (original urine) should be diluted with a buffer or an osmolarity compensating agent.

For example, the pH value of a urine sample, which has inherently a pH value of 4.5, can be adjusted to 8.0–8.5 by diluting said sample 2-fold or more with the reagent employed in the following Example.

In the method of the present invention, a fluorescent dye clearly stains, in particular, nucleic acids of cells in urine. As a result, fluorescent signal waves, as shown in FIGS. 2 to 6, are obtained. In FIGS. 2 to 6, wherein Auramine O was used as a fluorescent dye, erythrocytes free from nucleic acid were never stained with the fluorescent dye while leukocytes and epithelial cells having nuclei were stained particularly strongly in the nuclei. Thus bacteria, erythrocytes, leukocytes, epithelial cells and blood casts can be classified by setting two thresholds [refer to FIGS. 2 to 6(a) and (b)] or depending on the difference in signal pulse width. Table 2 shows the analytical conditions for each cell.

TABLE 2

Analytical conditions for each cell

|  | Cell size (µm) | Scattered light peak no. | Scattered light intensity | Fluorescence intensity |
|---|---|---|---|---|
| Erythrocyte | 3–10 | 1 | medium | weak |
| Leukocyte | 3–15 | 1 | medium | strong |
| Epithelial cell | 15–150 | 2 or more | strong/medium | strong |
| Blood cast | >100 | 2 or more | medium | weak/strong |
| Bacteria | 1–3 | 1 | weak | medium/weak |

Figure 7:
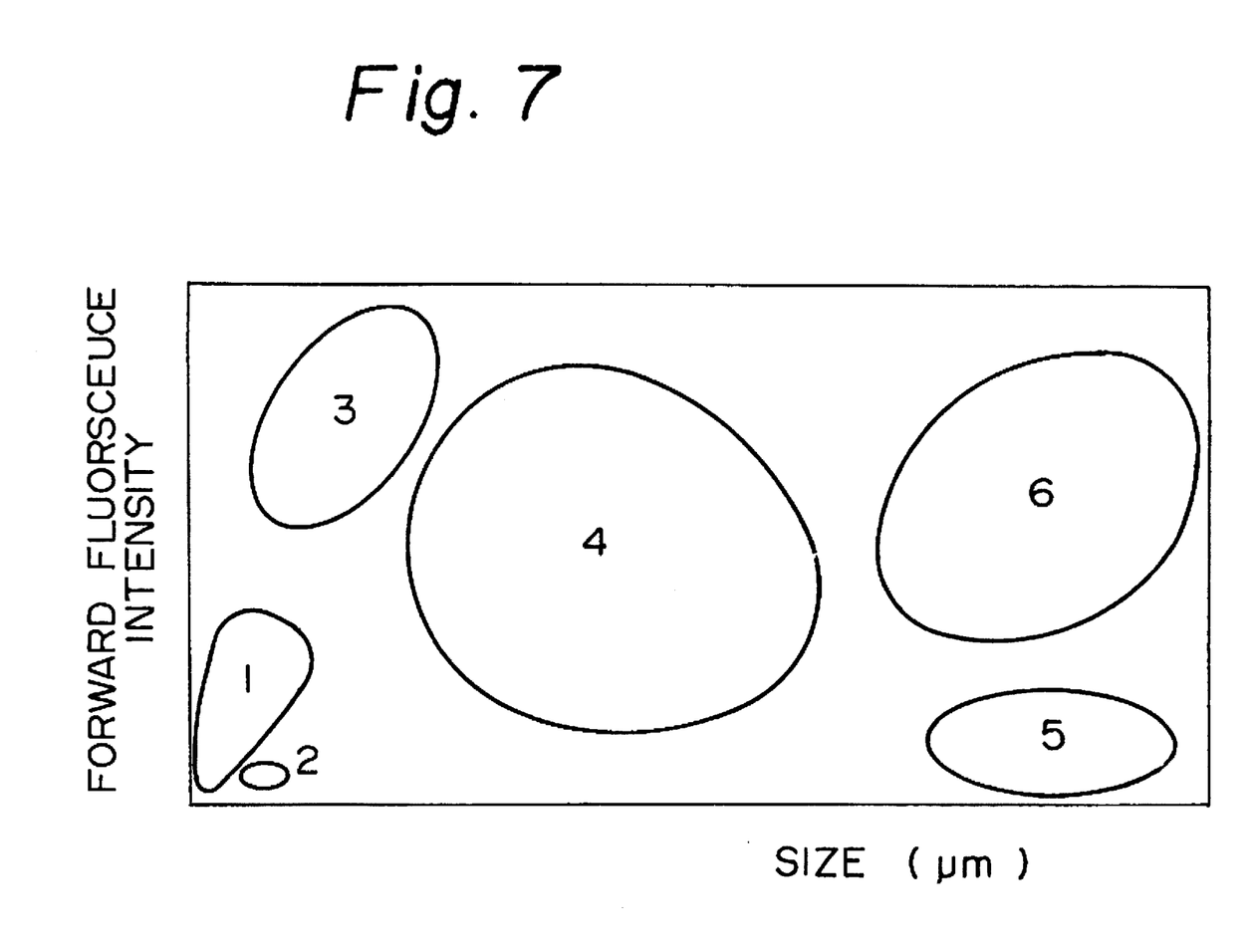
FIG. 7 is a model view of a scattergram showing the distribution of each cells which is formed by referring the abscissa to the size of each cell derived from the forward scattered light while referring the ordinate to the intensity of fluorescence of the cell.

Further, a scattergram as shown in FIG. 7 can be obtained by determining the size of each cell based on the pulse width of the signal wave of forward scattered light and comparing the fluorescence intensities of cells with each other. Thus the cells can be classified.

To further illustrate the present invention in greater detail, and not by way of limitation, the following Example will be given.

Example

Figure 8:
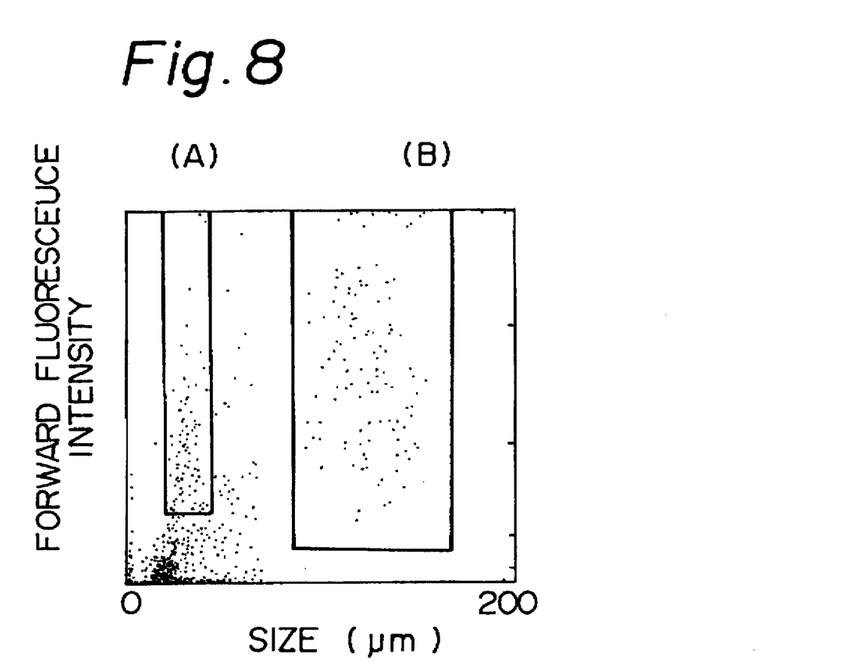
FIG. 8 is a scattergram showing the forward scattered light pulse width/the forward fluorescence intensity of cells in urine obtained by using a reagent which comprises Neutral Red as a fluorescent dye and adjusting the pH to 8.5 with a buffer.

A yellow brown reagent (pH 8.5) was prepared by mixing 30 ml of a 1,000 ppm aqueous solution of Neutral Red, 9.5 g of sodium propionate, 6.1 g of Tris and 7.4 g of Tricine, which were employed as buffers, and adjusting the total volume of the mixture to 1 l with water. 0.8 ml of a urine sample was added to 1.6 ml of the reagent obtained above to thereby give a urine specimen. After incubating at room temperature for 30 seconds, the specimen was fed into a flow cytometer. An argon ion laser capable of emitting excitation light of 488 nm was employed as a light source and fluorescence of 520 nm or above was detected. When the urine specimen, in which leukocytes and epithelial cells were visually observed, was analyzed with this cytometer, a scattergram of FIG. 8 was obtained and thus leukocytes and epithelial cells could be classified.

The reagent used in the above Example contained all of the fluorescent dye, buffer and osmolarity compensating agent. Alternately, these three components may be separately formulated into solutions. Then the reagents thus obtained may be simultaneously or successively added to a urine specimen. Thus results comparable to the above-mentioned ones can be obtained. When the reagent is divided into two or more packs, it is advantageous that the stabilities, in particular, that of a fluorescent dye can be improved and, as a result, the reagent can be easily preserved for a prolonged period of time. For example, some fluorescent dyes would decompose in the presence of an acid or an alkali (refer to, for example, Japanese Patent Laid-Open No. 35366/1989), which makes it difficult to preserve these fluorescent dyes in the form of an aqueous solution. In such a case, it is recommended that a fluorescent dye is previously dissolved in an organic solvent and then diluted with an aqueous solution containing a buffer and an osmolarity compensating agent immediately before the measurement, i.e., a two-pack type system.

Similarly, fluorescent dyes which are hardly soluble in water (for example, Rhodamine B) or precipitated or denatured at a certain pH level or salt concentration may be formulated into a two-pack type, or more, formulation so as to improve the keeping qualities of the reagent. When two or more fluorescent dyes are formulated into a single solution, furthermore, it is sometimes observed that the fluorescent dyes react with each other thus causing a deterioration in performance. In this case, it is also recommended to prepare a two-pack, or more, formulation so as to improve the keeping qualities of the reagent.

As described above, highly characteristic effects, as specified below, can be achieved by adding an appropriate amount of a reagent containing a fluorescent dye to a urine sample and measuring the obtained specimen by using a flow cytometer.

(1) No pretreatment (centrifuging, concentration) is required.

(2) The measurement can be rapidly completed.

(3) The measurement can be quantitatively and accurately effected.

(4) Bacteria, erythrocytes, leukocytes and epithelial cells can be easily classified depending on the difference in fluorescence intensity.

What is claimed is:

1. A method of classifying and counting cells in a urine specimen using flow cytometry comprising the steps of:

(a) diluting a urine sample 2 to 20 fold and staining nucleic acids of said cells with a reagent which comprises an aqueous solution containing:
  a fluorescent dye;
  a buffer; and
  an osmolarity compensating agent;

(b) irradiating said cells with light of violet or blue wavelength region by using a flow cytometer so as to obtain a scattered light signal wave and a fluorescent signal wave from each of said cells; and (c) measuring the scattered light signal wave and the fluorescent signal wave from each of said cells wherein said measuring step includes classifying and counting each of said cells by determining scattered light intensity, scattered light pulse width, scattered light peak number and fluorescence intensity.

2. A method according to claim 1, wherein blood corpuscles are separated from other cells depending on the difference in scattered light signal pulse width and then the blood corpuscles are further separated into erythrocytes and leukocytes depending on the difference in fluorescence intensity.

3. A method according to claim 1, wherein said fluorescent dye is one or more dyes selected from the group consisting of:

Auramine O;
Acridine Orange;
Ethidium bromide;
Propidium iodide;
Neutral Red;
Basic Yellow 11;
Acridine Red 3B;
Rhodamine S;
Rhodamine 6G;
Rhodamine B;
Rhodamine 19 perchlorate;
Rhodamine 123;
Eosin Y;
Cyanosine;
Cresyl Fast Violet;
Darrow Red;
Acronol Phloxine FFS;
3,3'-dimethylthiocarbocyanine;
3,3'-diethylthiocarbocyanine;
3,3'-diethyl-9-methylthiocarbocyanine bromide;
2-[γ-(1'-ethyl-4',5'-benzothiazolylidene) propenyl]-3-ethyl-4,5-benzoxazolium iodide;
Astrazon Red 6B;
Basic Violet 16;
2-(p-dimethylaminostyryl)-3-ethyl-4,5-benzothiazolium iodide;
2,4-bis(p-dimethylaminostyryl)-1-ethyl-pyridinium iodide;
2,6-bis(p-dimethylaminostyryl)-1-ethyl-pyridinium iodide; and
Astrazon Orange R.

4. A method according to claim 1, wherein said osmolarity compensating agent is selected from the group consisting of:
lithium chloride;
sodium chloride;
potassium chloride;
ammonium chloride;
sodium propionate;
phosphates; and
carbonates.

5. A method according to claim 1, wherein said buffer is selected from the group consisting of:
phosphoric acid (salt) series buffers;
phthalic acid (salt) series buffers;
citric acid (salt) series buffers;
boric acid (salt) series buffers;
acetic acid (salt) series buffers;
maleic acid (salt) series buffers;
Tris series buffers;
Tricine series buffers;
glycylglycine series buffers;
dimethylglycine series buffers;
diglycolic acid series buffers;
taurine series buffers; and
Barbital (salt) series buffers.

6. A method according to claim 1, wherein said reagent is in the form of one solution.

7. A method according to claim 1, wherein the contents of the aqueous solution are in the form of two or more solutions so as to secure the stability of the reagent.

8. A method according to claim 1, wherein the cells are analyzed without concentrating the urine.

9. The method according to claim 1 wherein the cells are erythrocytes, leukocytes, epithelial cells, blood cast and bacteria.

* * * * *